US00PP31723P2

(12) United States Plant Patent
Malinowski et al.

(10) Patent No.: US PP31,723 P2
(45) Date of Patent: May 5, 2020

(54) ***HIBISCUS* PLANT NAMED '15011 GR'**

(50) Latin Name: ***Hibiscus* hybrid (L.)**
Varietal Denomination: 15011 GR

(71) Applicant: The Texas A&M University System, College Station, TX (US)

(72) Inventors: Dariusz P. Malinowski, Vernon, TX (US); William E. Pinchak, Vernon, TX (US); R. Steve Brown, Vernon, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/501,695

(22) Filed: May 22, 2019

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./257
CPC ..... A01H 5/02; A01H 6/60
See application file for complete search history.

(56) References Cited

PUBLICATIONS

U.S. Appl. No. 16/501,691, filed May 22, 2019, Malinowski et al.
U.S. Appl. No. 16/501,698, filed May 22, 2019, Malinowski et al.
U.S. Appl. No. 16/501,696, filed May 22, 2019, Malinowski et al.
U.S. Appl. No. 16/501,693, filed May 22, 2019, Malinowski et al.
U.S. Appl. No. 16/501,694, filed May 22, 2019, Malinowski et al.
U.S. Appl. No. 16/501,692, filed May 22, 2019, Malinowski et al.
U.S. Appl. No. 16/501,697, filed May 22, 2019, Malinowski et al.
"*Hibiscus* Luna TM White," PanAmerican Seed, <https://www.panamseed.com/plant_info.aspx?phid=033102347005863>, accessed on Aug. 26, 2019.

*Primary Examiner* — Annette H Para
(74) *Attorney, Agent, or Firm* — Dentons US LLP

(57) ABSTRACT

'15011 GR' is a new and distinct hardy herbaceous *Hibiscus* hybrid with novel characteristics that include upright branched stems, numerous, outward-facing, near white, lighter than yellowish white flowers with a light purplish pink blush and a center eye that is nearest strong purplish red, a prolonged blooming season, petals with indented top margins, and hastate, trilobed leaves.

4 Drawing Sheets

Latin name of the genus and species of the plant claimed: *Hibiscus* hybrid (L.).

Cultivar denomination: '15011 GR'.

BACKGROUND OF THE INVENTION

The invention relates to the new and distinct *hibiscus* plant '15011 GR'. '15011 GR' was generated from a cross performed on Jul. 18, 2014 near Vernon, Tex. between '10054-6' (pod parent, unpatented) and '10054-4' (pollen parent, unpatented). The pedigrees of each parent reflect a complex mixture of *hibiscus* species that include, for example, *H. mocheutos, H. coccineus*, or *H. militaris*. The seed from this cross was harvested on Aug. 30, 2014 and the '15011 GR' seedling was selected in the summer of 2015. '15011 GR' was first asexually propagated near Vernon, Tex. in 2016 by stem tip cuttings. The resulting as well as subsequent asexually propagated plants have been stable and true to type throughout successive generations.

SUMMARY OF THE INVENTION

'15011 GR' differs from its parents and all other known hardy herbaceous *hibiscus* plants. The following are the most outstanding and distinguishing characteristics of '15011 GR': (1) it is a hardy perennial with dense branching and a compact growth habit; (2) it blooms profusely over a prolonged season; and (3) its flowers exhibit a near white (lighter than yellowish white RHS 155D) background with a light purplish pink (RHS 65B) blush that develops as the flower matures during the day, a center eye that is nearest strong purplish red (RHS 71B), and petals with indented top margins.

'15011 GR' plants can be readily and unambiguously distinguished from those of its parents. '15011 GR' plants exhibit near white (lighter than yellowish white RHS 155D) flowers that have an average diameter of 18 cm and a light purplish pink (RHS 65B) blush that develops as the flower matures during the day, a nearest strong purplish red (RHS 71B) eye, and petals with indented top margins and hastate leaves with indented margins. Whereas, '10054-6' plants (pod parent) exhibit moderate purplish pink (RHS 62B) flowers that have an average diameter of 20 cm and distinctive white (lighter than yellowish white RHS 155D) veins, a strong purplish red (RHS 61B) eye, and petals with indented top margins and ovate leaves with slightly indented margins; and '10054-4' plants (pollen parent) exhibit light purplish pink (RHS 62C) flowers that have an average diameter of 18 cm and distinctive white (lighter than yellowish white RHS 155D) veins and a strong purplish red (RHS 61B) eye and ovate leaves with slightly indented margins.

'PAS304889' is the *hibiscus* plant that exhibits flowers that are colored most similarly to those of '15011 GR'. Nonetheless, plants of '15011 GR' and 'PAS304889' can also be readily and unambiguously distinguished from one another at least based upon petal shape, flowering amount, and flowering time. The petals of '15011 GR' have indented top margins; whereas, the petals of 'PAS304889' do not have indented top margins. Also, plants of '15011 GR' display slightly more elongated petals, earlier flowering, and more profuse flowering than plants of 'PAS304889'.

BRIEF DESCRIPTION OF THE DRAWINGS

'15011 GR' is illustrated by the accompanying photographs, which show the plant's form and foliage. The colors shown are as true as can be reasonably obtained by conventional photographic procedures.

DETAILED BOTANICAL DESCRIPTION

Figure 1:
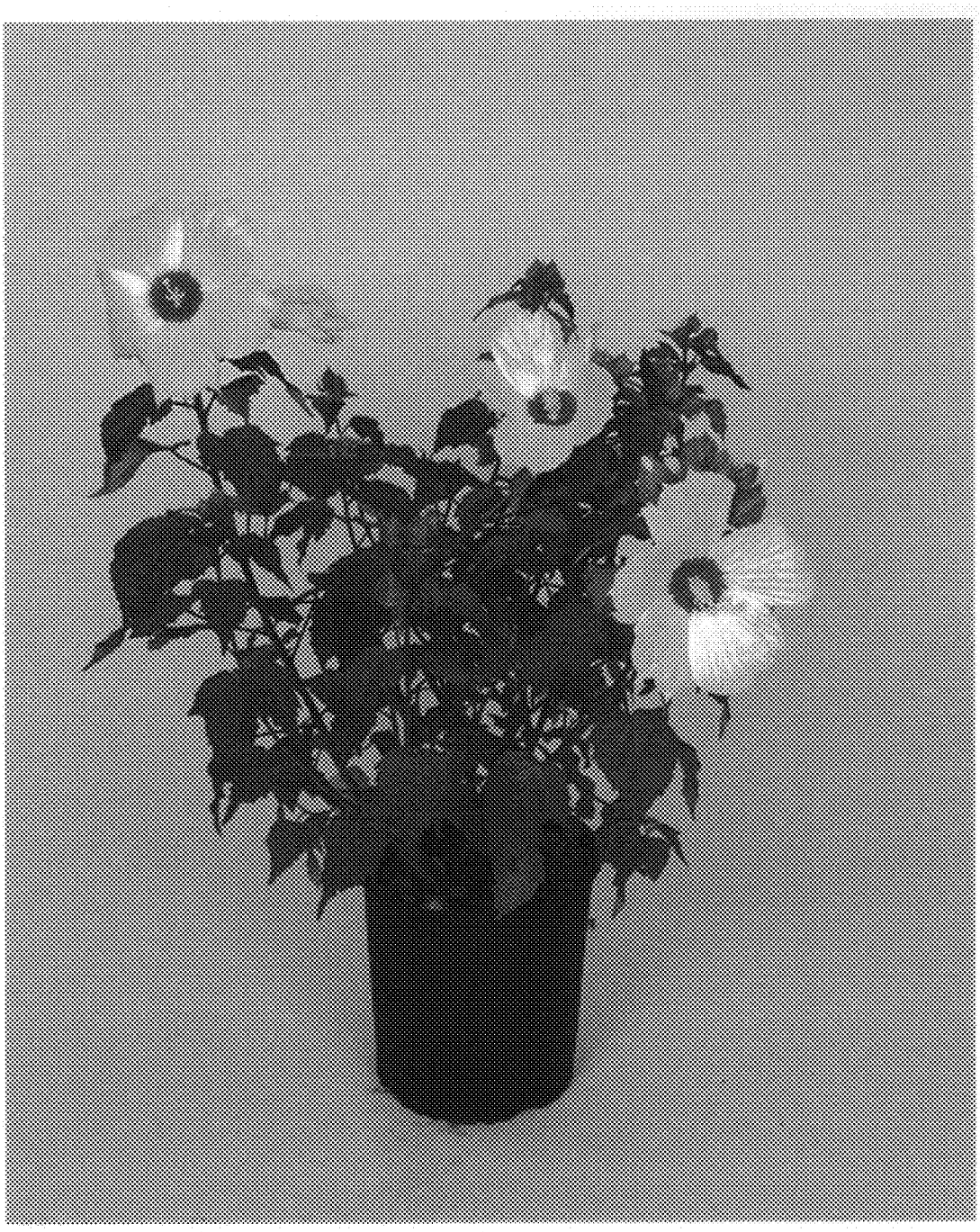
FIG. 1—Shows a 6-week-old '15011 GR' plant in a container.
Figure 2:
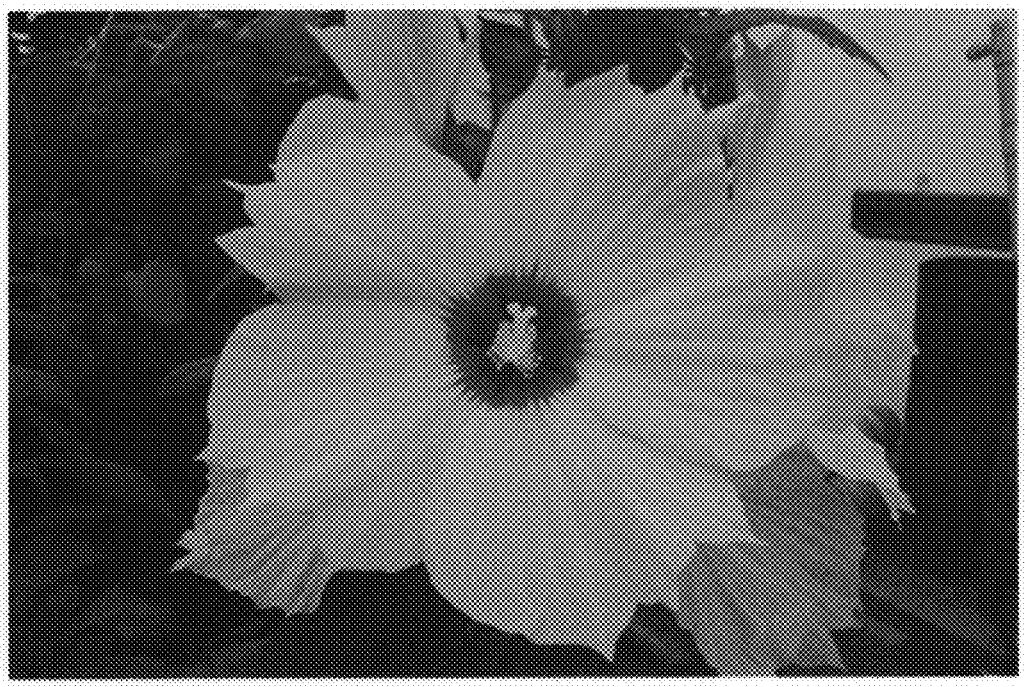
FIG. 2—Shows a '15011 GR' flower as seen looking directly at the adaxial surface of the petals on a 2-year-old plant.
Figure 3:
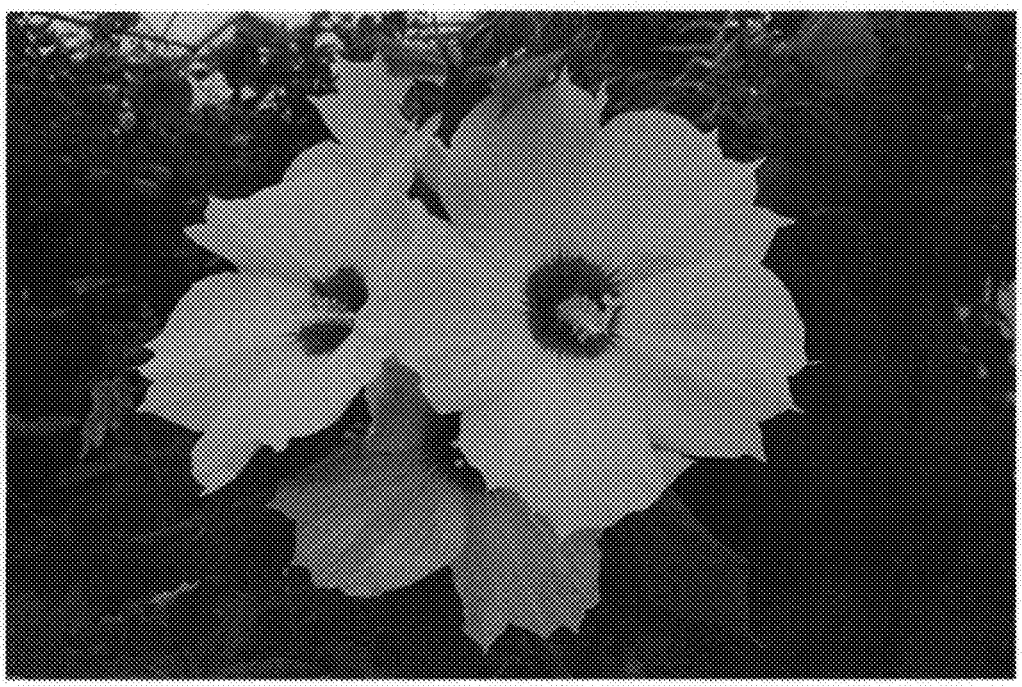
FIG. 3—Shows '15011 GR' flowers as seen looking slightly askew from the adaxial surface of the petals on a 2-year-old plant.
Figure 4:
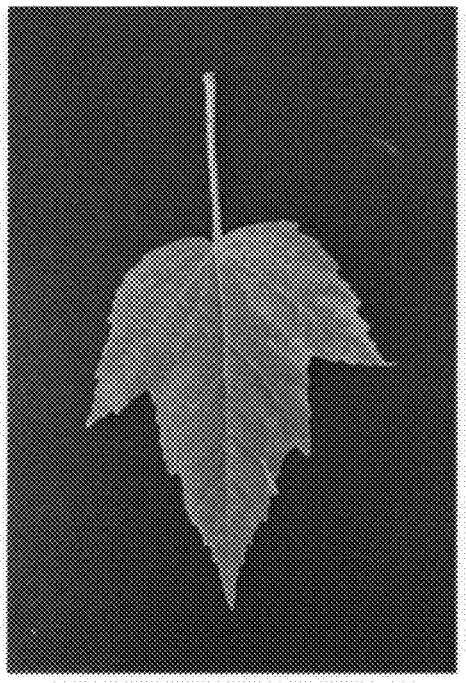
FIG. 4—Shows a '15011 GR' leaf.

The following detailed description sets forth the distinctive characteristics of '15011 GR'. The detailed description was obtained using two-year-old plants grown in loamy sand, open-field, full sun trials at a nursery near Vernon, Tex., during which the plants were supplemented with fertilizer and water as needed. These plants are natural habit and were not treated with plant growth regulators and they were not pinched at any time in the growth year. '15011 GR' has not been observed under all possible environments, and certain characteristics may vary slightly under different environmental conditions. Color references are to The Royal Horticultural Society Colour Chart of The Royal Horticultural Society of London (R.H.S.), 2001 ($4^{th}$ edition).

Propagation:

*Method.*—Stem cuttings.

*Time to initiate roots from stem cuttings after treating cuttings with a commercial rooting hormone.*—About 2 weeks under misting and at an air temperature of 85° C.

*Rooting habit.*—Normal, branching, fleshy, and developing a thick diameter (to about 2.5 cm).

*Root color.*—Pale yellow (between RHS 161D and RHS 162D), depending on soil type.

*Crop time (under normal summer growing conditions and when grown in a 4 L container from a rooted cutting).*—8 to 10 weeks to flower with very good plant vigor.

Plant:

*Plant shape and habit.*—Hardy herbaceous perennial with 8 to 10 thick upright and heavily branched main stems producing an upright spreading mound about 100 cm tall and 95 cm wide, which is widest about 50 cm above the soil line

*Primary branches.*—8 to 10 per main stem that protrude at about a 45° angle from horizontal.

*Lateral branches.*—On the middle half of the primary stems.

*Lateral branch size.*—Between 10 cm and 25 cm long (shorter at the upper nodes) and with an average diameter of 8.0 mm at their base.

*Flower location.*—Upper ⅓ of the plant beginning at axillary nodes while still developing at the apex.

*Stem.*—Rounded, glabrous; averages about 100 cm tall and 3.5 cm diameter their base.

*Stem color.*—Near dark reddish orange (RHS 173A).

*Internode.*—About 16 nodes per stem below flower and about 32 total, average internode length about 4.0 cm of unpinched plant, but varies between 2.0 to 5.0 cm and are widest in middle portion of stem.

Foliage:

*Shape.*—Leaves hastate, trilobed with indented margins.

*Texture.*—Adaxial and abaxial matte.

*Leaf blade size.*—To about 14.0 cm long and 8.0 cm wide, larger proximally and becoming smaller in distal portion of stem.

*Foliage color.*—Adaxial and abaxial strong yellowish green (RHS 135C) with dark reddish orange (RHS 173A) tint when exposed to high sunlight.

*Veins.*—Palmate; adaxial and abaxial veins dark reddish orange (RHS 173A).

*Petiole size (average).*—9.0 cm long and 5.0 mm wide.

*Petiole color.*—Dark reddish orange (RHS 173A).

Flowers:

*Buds.*—One day prior to opening about 3.5 cm long and 2.5 cm in diameter, pointed apex and bluntly rounded base; and, prior to showing petals, about 4.0 cm long and 2.5 cm in diameter, ovoid with acute apex.

*Bud color.*—Exposed petal near white (lighter than yellowish white RHS 155D); and, prior to showing petals, near white (lighter than yellowish white (RHS 155D).

*Epicalyx.*—Entire, smooth, puberulent both surfaces, linear with sharply acute apex and attenuate base, curved around sepals; typically 10 to 12 per flower; about 2.5 cm long tapering to base of about 3.0 mm wide.

*Epicalyx color.*—Adaxial and abaxial strong yellowish green (RHS 135C).

*Sepals.*—5, proximal half connate forming campanulate star-shaped calyx; acute apex; margin entire, edentate; puberulent abaxial glabrous adaxial; individually about 3.5 cm long and about 2.5 cm wide at fusion point. From the upper side of the flower, sepals visible as a star shape in the center of the flower.

*Sepal color.*—Abaxial and adaxial color strong yellowish green (RHS 135C).

*Flowers.*—Solitary, about 20 to 30 per main stem without pinching; primarily outwardly facing; average 18 cm across, larger in early part of flowering season; persist for one to two days, depending on temperature; effective for at least 14 weeks beginning early July and lasting into October (north Texas), no detectable fragrance.

*Petals.*—5; glabrous, dull both front and back toward middle and perimeter, adnate to the androecium to form a column, slightly imbricate to about 15% overlapping at widest part (petals about 30% overlapping the next petal to either side). Veins: Parallelly veined, veins near white (lighter than yellowish white RHS 155D), impressed on front and ribbed on back; veins extend from the eye zone and have strong purplish red (RHS 71B) color of the beginning 1.0 cm distance, then change to near white (lighter than yellowish white RHS 155D). Shape:

Rounded. Margins: Indented with 2-4 distinctive teeth. Apex: Rounded. Base: Short claw-like. Surface: Adaxial and abaxial glabrous, ribbed. Size (average): About 10.0 cm long and about 8.0 cm wide at widest portion (largest in earlier part of flowering season); center dark eye about 4.0 cm diameter. Color: Adaxial and abaxial near white (lighter than yellowish white RHS 155D), having light purplish pink (RHS 65B) blush as the flower matures during the day; center eye nearest strong purplish red (RHS 71B).

*Gynoecium*.—Style: Enclosed in column about 4.5 cm long and 0.5 cm wide at base; near white (lighter than yellowish white RHS 155D); style protruding from column and split in distal 10.0 mm portion into typically 5 branches, branch diameter 2.0 mm; near white (lighter than yellowish white RHS 155D). Stigma: Typically 5; globose, puberulose, about 3.0 mm in diameter; near white (lighter than yellowish white RHS 155D). Ovary: Superior, about 6.5 mm across at base and 6.0 mm tall; acute apex.

*Androecium*.—Filaments: Numerous, about 160; less than 1.0 mm in diameter and about 5.0 mm long; attached along nearly the entire length of column; near white (lighter than yellowish white RHS 155D). Anthers: Reniform; about 2 mm long and 1 mm wide; near white (lighter than yellowish white RHS 155D). Pollen: Numerous, globose, less than 0.1mm long; near white, (lighter than yellowish white RHS 155D).

*Pedicel*.—Rounded in cross section, finely puberulent; length from base of sepal to abscission point average 1.5 cm long and 3.5 mm wide; color brilliant yellowish green (RHS 135C).

*Peduncle*.—Rounded, puberulent, average about 6.0 cm long from abscission point to stem and 4.0 mm wide, slightly longer on earlier flowers.

*Peduncle color*.—Near dark reddish orange (RHS 173A).

*Fruit*.—Few, loculicidal capsule; glabrous; globose, occasionally with abruptly acute apex; color between light yellowish brown (RHS 199C) and dark grayish yellow (RHS 199D) when mature.

*Seed*.—Minutely floccose, typically globose; about 3.0 mm in diameter; color between dark grayish reddish brown (RHS 200A) and moderate brown (RHS 200C).

Resistance: The plant grows best with plenty of moisture, but is able to tolerate some drought once established. Other pest and disease resistance beyond that of other hardy perennial *hibiscus* cultivars has not been observed. Hardiness at least from USDA Zone 4 through 9.

Commercial use: Suitable for potted plant culture, landscaping as a specimen or en masse, and especially suited for patios and confined spaces because of the compact habit.

What is claimed is:

1. A new and distinct *Hibiscus* hybrid (L.) plant named '15011 GR' as shown and described herein.

* * * * *